US00PP19263P2

(12) United States Plant Patent
Meilland

(10) Patent No.: US PP19,263 P2
(45) Date of Patent: Sep. 23, 2008

(54) CLIMBING ROSE PLANT NAMED 'MEIVANERY'

(50) Latin Name: *Rosa hybrida* Climbing rose
Varietal Denomination: Meivanery

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/905,489

(22) Filed: Oct. 1, 2007

(51) Int. Cl.
*A01H 5/00* (2006.01)

(52) U.S. Cl. ..... Plt./111

(58) Field of Classification Search ..... Plt./111, Plt./101, 109
See application file for complete search history.

*Primary Examiner*—Annette H Para
*Assistant Examiner*—S. B. McCormick-Ewoldt
(74) *Attorney, Agent, or Firm*—Buchanan Ingersoll & Rooney PC

(57) ABSTRACT

A new and distinct variety of Climbing rose plant is provided which abundantly forms attractive yellow blossoms having a slight fragrance and the configuration of an old rose. The plant displays good vigor and good tolerance to diseases, particularly with respect to Black Spot. The foliage is very dense and semi-glossy, and contrasts nicely with the blossom coloration. The new variety is particularly well suited for growing as attractive ornamentation in the landscape where a climping rose plant is desired.

1 Drawing Sheet

Figures 1, 2, 3, 4, 5, 6, 7, 8, 9, 10, 11, 12, 13, 14, 15, 16:
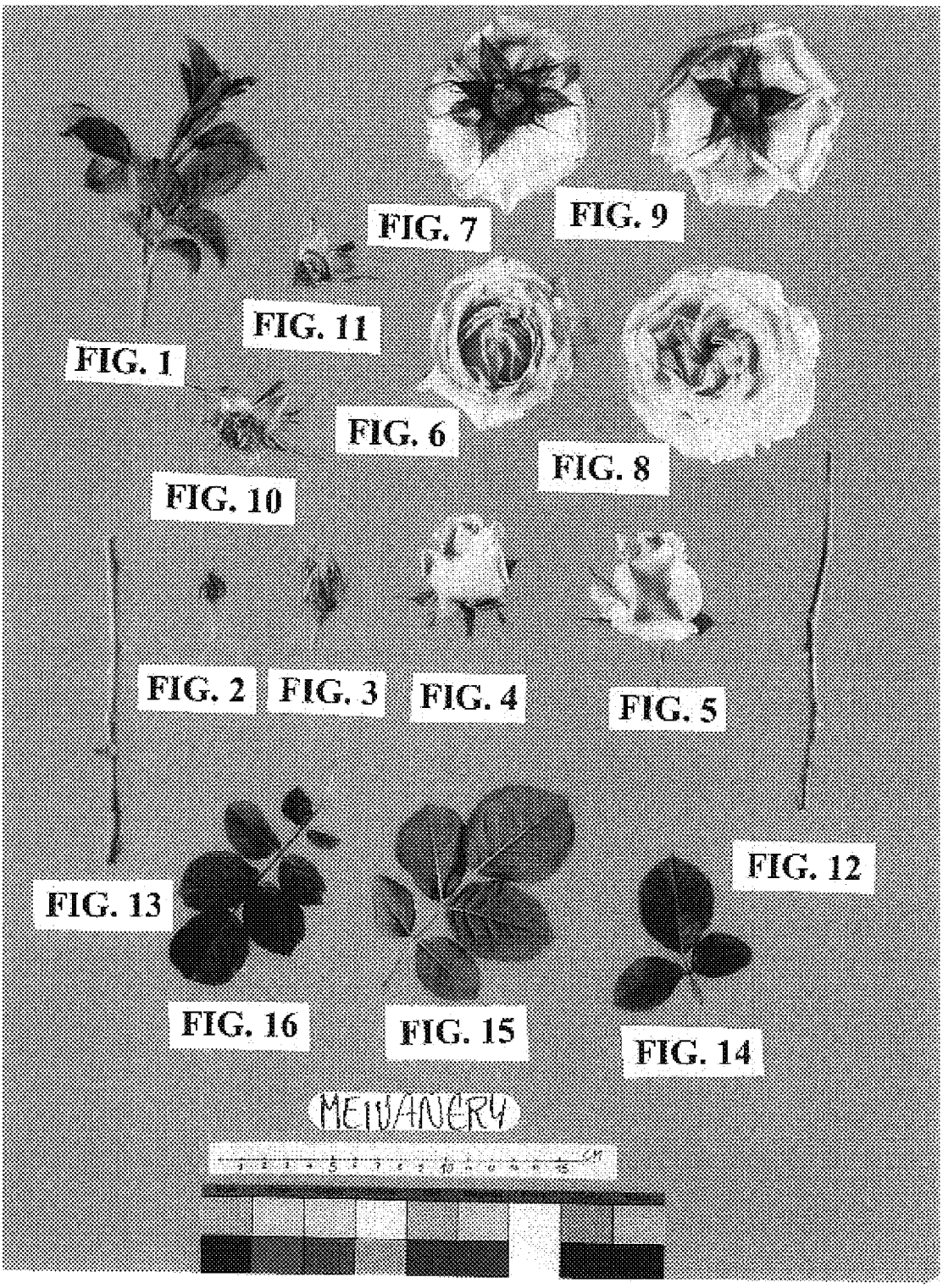

Botanical/commercial classification: *Rosa hybrida*/ Climbing Rose.
Varietal denomination: cv. Meivanery.

SUMMARY OF THE INVENTION

The new variety of *Rosa hybrida* Climbing rose plant was discovered during June 1999, at Le Cannet des Maures, Var, France, while growing among plants of the 'Meitosier' variety (U.S. Plant Pat. No. 9,233). The new variety was found to display a distinctive blossom coloration unlike that of the 'Meitosier' variety, and is believed to be a spontaneous mutation of unknown causation of such variety. The blossoms of the new variety exhibit an attractive yellow coloration unlike the light Mandarin Orange blossom coloration of the 'Meitosier' variety. Had the new variety of the present invention not been discovered and preserved, it would have been lost to mankind.

It was found that the new rose variety of the present invention:

(a) exhibits a climbing growth habit, (b) abundantly forms on a substantially continuous basis attractive yellow blossoms having a slight fragrance and the configuration of an old rose, (c) forms very dense semi-glossy foliage that contrasts well with the blossom coloration, (d) displays good vigor, (e) displays good disease tolerance, particularly with respect to Black Spot, and (f) is particularly well suited for growing as attractive ornamentation in the landscape.

The new variety well meets the needs of the horticultural industry and can be used to advantage for growing in the landscape where an attractive climbing rose plant is desired.

The new variety of the present invention can be readily distinguished from its 'Meitosier' parent variety through a comparison of the blossom colorations that are displayed.

The new variety has been found to undergo asexual propagation in France by a number of routes, including budding, grafting, and cuttage. Asexual propagation by the abovementioned techniques in France has shown that the characteristics of the new variety are stable and are strictly transmissible by such asexual propagation from one generation to another.

The new variety has been named the 'Meivanery' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during July while budded on *Rosa froebelii* understock and growing outdoors at Le Cannet des Maures, Var, France. Dimensions in centimeters and a standard color presentation are indicated at the bottom of the photograph.

FIG. 1 - illustrates a specimen of a young shoot;

FIG. 2 - illustrates a specimen of a floral bud before the opening of the sepals;

FIG. 3 - illustrates a specimen of a floral bud at the opening of the sepals;

FIG. 4 - illustrates a specimen of a floral bud at the opening of the petals;

FIG. 5 - illustrates a specimen of a flower in the course of opening;

FIG. 6 - illustrates a specimen of an open flower — plan view — obverse;

FIG. 7 - illustrates a specimen of an open flower — plan view — reverse;

FIG. 8 - illustrates a specimen of a fully open flower — plan view — observe;

FIG. 9 - illustrates a specimen of a fully open flower — plan view — reverse;

FIG. 10 - illustrates a specimen of a floral receptacle showing the arrangement of the stamens and pistils;

FIG. 11 - illustrates a specimen of a floral receptacle showing the arrangement of the pistils (stamens removed);

FIG. 12 - illustrates a specimen of a flowering stem;

FIG. 13 - illustrates a specimen of a main branch;

FIG. 14 - illustrates a specimen of a leaf with three leaflets — plan view — upper surface;

FIG. 15 - illustrates a specimen of a leaf with five leaflets — plan view — under surface; and FIG. 16 - illustrates a specimen of a leaf with seven leaflets — plan view — upper surface.

DETAILED DESCRIPTION

The chart used in the identification of the colors is that of The Royal Horticultural Society (R.H.S. Colour Chart). The description is based on the observation of one-year-old plants during July while budded on *Rosa froebelii* understock and growing outdoors at Le Cannet des Maures, Var, France.

Class: Climbing.

Plant:

*Height.*—Approximately 180 cm on average at the end of the growing season.

*Width.*—Approximately 80 cm on average at the end of the growing season.

*Habit.*—Climbing.

Branches:

*Color.*—Young stems: near Yellow-Green Group 144A. Adult wood: near Green Group 139A.

*Thorns.*—Size: variable (as illustrated), with the longest thorns commonly being approximately 10 mm in length. Quantity: an adult stem having a length of 10 cm commonly will bear approximately 4 smaller thorns having lengths of approximately 8 mm on average, and an adult stem having a length of approximately 15 cm commonly will bear approximately 7 longer thorns having a length of approximately 10 mm on average. Configuration: rather straight longish-pointed on upper surface and slightly concave on the under surface (as illustrated). Color: on adult stems the smaller thorns commonly are near Greyed-Orange Group 164B in coloration and the longer thorns commonly are near Yellow-Green Group 144C. Base: commonly narrow obovate for smaller thorns and broad ovate for longer thorns.

Leaves:

*Stipules.*—Adnate, pectinate, smooth, broad, approximately 2 cm in length on average and approximately 0.6 cm in width on average, and near Green Group 137B on the upper surface and near Green Group 138B on the under surface.

*Petioles.*—Length: approximately 3.1 cm for terminal leaflet. Color: near Green Group 137C on the upper surface and near Green Group 138B on the under surface.

*Rachis.*—Color: near Green Group 137D on the upper surface and near Green Group 138B on the under surface.

*Leaflets.*—Number: 3, 5 (most often), and 7. Shape: somewhat ovate with an obtuse base and an acuminate tip. Size: terminal leaflets commonly are approximately 4.7 cm in length and approximately 3.8 cm in width. Serration: small and single (as illustrated). Texture: smooth and fairly thick. General appearance: very dense, and medium green with a semi-glossy aspect. Color (young foliage): Upper surface: near Yellow-Green Group 144. Under surface: near Yellow-Green Group 146C. Color (adult foliage): Upper surface: near Green Group 137A. Under surface: near Green Group 138B.

Inflorescence

*Number of flowers.*—Commonly in clusters of 1 to 5 flowers per stem.

*Sepals.*—Five in number, tomentose on the upper surface, smooth on the under surface, elongated, approximately 1.7 cm in length, approximately 1.3 cm in width, longish-pointed and somewhat narrow, with a slightly rounded base, two sepals commonly possess no extensions, three sepals commonly possess very weak extensions, near Green Group 139D in coloration on the upper surface, near Yellow-Green Group 144C on the under surface.

*Peduncles.*—Length: approximately 3 cm on average. Diameter: approximately 0.4 cm on average. Texture: glandular. Color: near Yellow-Green Group 144C.

*Buds.*—Shape: globular. Size: medium (as illustrated). Length: approximately 1.8 cm on average. Width: approximately 2 cm on average. Color (as the calyx breaks): upper surface: near Dresden Yellow, Yellow Group 5C. Under surface: near Dresden Yellow, Yellow Group 5D.

*Flower.*—Shape: flat-cupped. Diameter: approximately 9 cm when open on average. Color (in course of opening): upper surface: near Dresden Yellow, Yellow Group 5C. Under surface: near Dresden Yellow, Yellow Group 5D. Spot at base: absent. Color (open flower): Upper surface: Primrose Yellow, Yellow Group 4C. Under surface: Primrose Yellow, Yellow Group 4C. Spot at base: absent. Fragrance: slight. Petal number: approximately 90 to 100 on average under normal growing conditions. Petal arrangement: imbricated. Petal length: approximately 4 cm on average. Petal width: approximately 3.3 cm on average. Petal shape: with a generally rounded tip and an obovate base. Petal texture: physically somewhat firm. Petaloids: none formed. Petal drop: good with the petals commonly detaching cleanly before drying. Anthers: arranged regularly around the styles, approximately 117 in number on average, approximately 0.3 cm in size, and near Yellow-Orange Group 14A in coloration. Filaments: approximately 0.9 cm in length and near Orange-Red Group 31A in coloration. Stigma: approximately 0.13 cm in size on average, and near Yellow-Green Group 145B in coloration. Styles: approximately 176 in number on average, approximately 0.2 cm in length, and near White Group 155B in coloration. Receptacle: funnel-shaped in longitudinal section, smooth in texture, approximately 0.7 cm in length on average, and approximately 1.4 cm in width on average, and near Green Group 143C in coloration. Hips: none observed during observations to date.

Longevity: a typical blossom commonly lasts approximately 12 days on average on the plant. The longevity of the blossoms when cut and placed in a vase has not been evaluated since the variety is primarily intended for growing in the garden.

Development:

*Vegetation.*—Very strong.

*Blooming.*—Mid-season, abundant and nearly continuous.

*Tolerance to diseases.*—Good, particularly with respect to Black Spot.

I claim:

1. A new and distinct variety of rose plant characterized by the following combination of characteristics:

(a) exhibits a climbing growth habit, (b) abundantly forms on a substantially continuous basis attractive yellow blossoms having a slight fragrance and the configuration of an old rose, (c) forms very dense semi-glossy foliage that contrasts well with the blossom coloration, (d) displays good vigor.

(e) displays good disease tolerance, particularly with respect to Black Spot, and (f) is particularly well suited for growing as attractive ornamentation in the landscape;

substantially as herein shown and described.

* * * * *

MEINANERY